US012805881B2

(12) United States Patent
O'Sullivan

(10) Patent No.: US 12,805,881 B2
(45) Date of Patent: Nov. 24, 2026

(54) SPHEROIDAL SURGICAL RASP

(71) Applicant: Stryker European Operations Limited, Carrigtwohill (IE)

(72) Inventor: Denis O'Sullivan, Cloughoulamore (IE)

(73) Assignee: Stryker European Operations Limited, Carrigtwohill (IE)

( * ) Notice: Subject to any disclaimer, the term of this patent is extended or adjusted under 35 U.S.C. 154(b) by 536 days.

(21) Appl. No.: 17/759,812

(22) PCT Filed: Jan. 28, 2021

(86) PCT No.: PCT/IB2021/050669
§ 371 (c)(1),
(2) Date: Jul. 29, 2022

(87) PCT Pub. No.: WO2021/152498
PCT Pub. Date: Aug. 5, 2021

(65) Prior Publication Data

US 2023/0065055 A1 Mar. 2, 2023

Related U.S. Application Data

(60) Provisional application No. 62/967,771, filed on Jan. 30, 2020.

(51) Int. Cl.
*A61B 17/16* (2006.01)
*A61C 1/12* (2006.01)
(Continued)

(52) U.S. Cl.
CPC ...... *A61B 17/1659* (2013.01); *A61B 17/1628* (2013.01); *A61B 17/1631* (2013.01);
(Continued)

(58) Field of Classification Search
CPC ............ A61B 17/1659; A61B 17/1628; A61B 17/1631; A61B 17/1682; A61B 17/162;
(Continued)

(56) References Cited

U.S. PATENT DOCUMENTS 5,318,570 A * 6/1994 Hood ................ A61B 17/8847
601/2
5,725,531 A 3/1998 Shapiro
(Continued)

OTHER PUBLICATIONS

International Search Report for Application No. PCT/IB2021/050669 dated Mar. 12, 2021, 2 pages.

*Primary Examiner* — Marcela I. Shirsat
(74) *Attorney, Agent, or Firm* — Howard & Howard Attorneys PLLC

(57) ABSTRACT

A rasp for use with a powered surgical handpiece comprises opposed proximal and distal ends and a rasp region. The proximal end includes a mount portion. The mount portion defines a pivot axis. The rasp region extends between the mount portion and the distal end and includes the distal end. The rasp region has opposed first and second surfaces connecting at a common edge. The first surface is convex and the second surface is concave. The rasp region has a plurality of cutting projections disposed on at least one of the first surface and the second surface. The rasp region has a center axis substantially parallel to the pivot axis.

19 Claims, 17 Drawing Sheets

(51) Int. Cl.
*A61C 1/14* (2006.01)
*A61C 3/03* (2006.01)
*A61C 3/06* (2006.01)

(52) U.S. Cl.
CPC ......... *A61B 17/162* (2013.01); *A61B 17/1622* (2013.01); *A61B 17/1657* (2013.01); *A61B 17/1662* (2013.01); *A61B 17/1664* (2013.01); *A61B 17/1666* (2013.01); *A61B 17/1668* (2013.01); *A61B 17/1675* (2013.01); *A61B 17/1682* (2013.01); *A61B 17/1684* (2013.01); *A61C 1/12* (2013.01); *A61C 1/141* (2013.01); *A61C 1/148* (2013.01); *A61C 3/03* (2013.01); *A61C 3/06* (2013.01); *Y10T 29/44* (2015.01); *Y10T 407/1815* (2015.01); *Y10T 407/19* (2015.01)

(58) Field of Classification Search
CPC ............ A61B 17/1622; A61B 17/1662; A61B 17/1664; A61B 17/1675; A61B 17/1615; A61B 17/16; A61B 17/1602; A61B 17/1617; A61B 17/1635; A61B 17/1637; A61B 17/164; A61B 17/1642; A61B 17/1657; A61B 17/1666; A61B 17/1668; A61B 17/1684; A45D 29/06; Y10T 407/1815; Y10T 407/19; Y10T 29/44; A61C 1/10; A61C 1/12; A61C 1/141; A61C 1/145; A61C 1/147; A61C 1/148; A61C 3/03; A61C 3/06; A61C 3/12; A61C 5/42; B23B 45/00; B23B 49/005; B25B 21/002
USPC ........ 606/85, 89, 80, 84, 81; 132/76.4, 76.5, 132/75.6, 75.3, 73.5; 433/142; 407/29.15, 29.13, 29.1
See application file for complete search history.

(56) References Cited

U.S. PATENT DOCUMENTS

| | | | | |
|---|---|---|---|---|
| 2005/0015153 | A1 * | 1/2005 | Goble .................. | A61F 2/3859 606/88 |
| 2006/0025776 | A1 * | 2/2006 | Thorsgard .......... | A61B 17/1637 606/96 |
| 2006/0089650 | A1 | 4/2006 | Nolde | |
| 2011/0270256 | A1 * | 11/2011 | Nelson ............... | A61B 17/1659 606/85 |
| 2013/0304070 | A1 * | 11/2013 | Nelson ............... | A61B 17/1624 606/85 |
| 2018/0125503 | A1 * | 5/2018 | Sidebotham ......... | A61B 17/147 |

* cited by examiner

SPHEROIDAL SURGICAL RASP

CROSS-REFERENCE TO RELATED APPLICATIONS

The subject patent application is a National Stage application of International Application No PCT/IB2021/050669, filed on Jan. 28, 2021, which claims priority to, and all the benefits of, United States Provisional Patent Application No. 62/967,771, filed on Jan. 30, 2020, the entire contents of which are incorporated by reference herein.

BACKGROUND

A tool that facilitates preparation of facing ends of bones that are to be joined to each other is desired.

DETAILED DESCRIPTION

Figure 1:
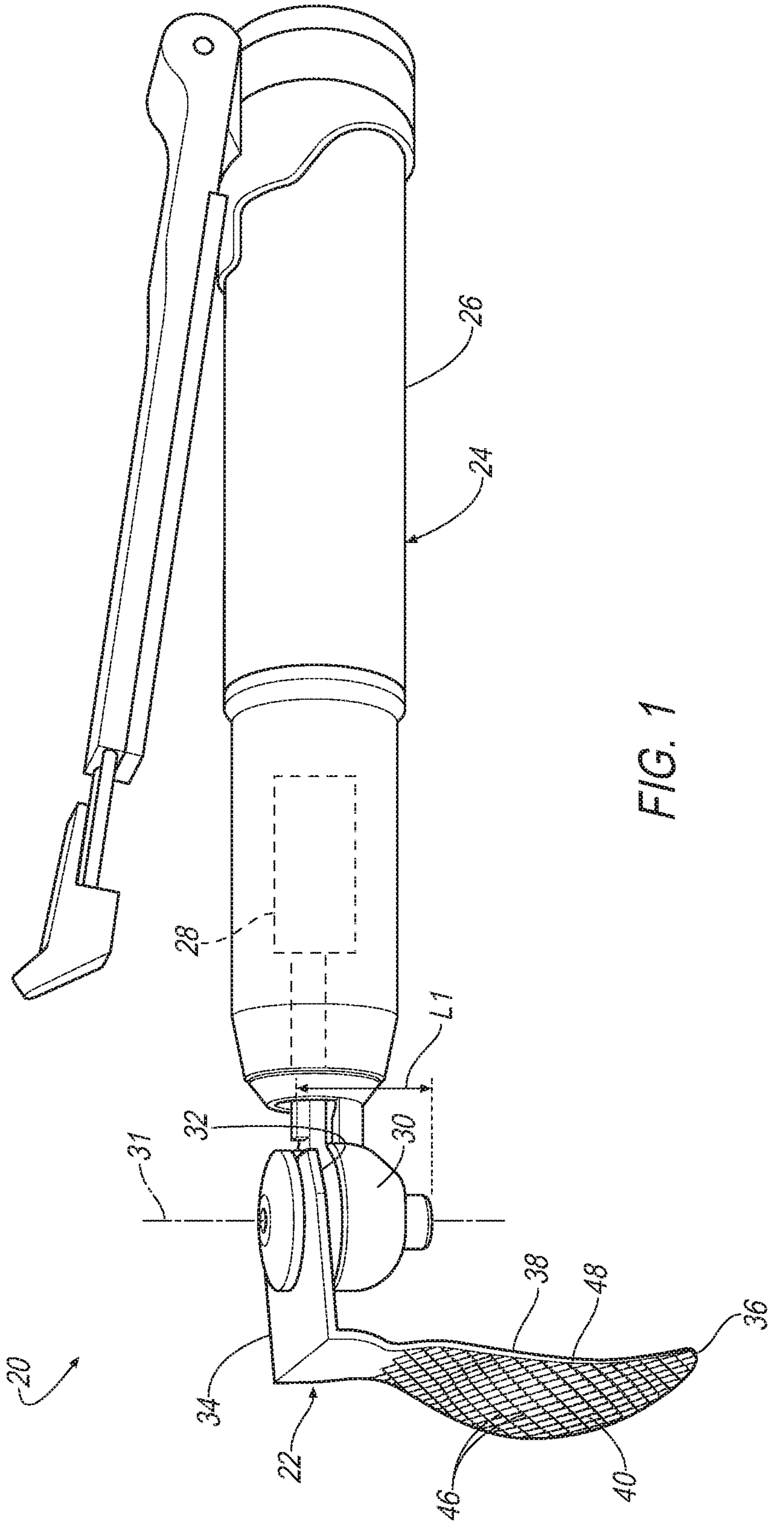
FIG. 1 is a perspective view of a first example surgical rasp having a first example shape mounted on a first example surgical handpiece.

The prior art does not address the need to provide a rasp that facilitates preparation of facing ends of bones that may be joined or alternatively stated, fused, to each other.

A rasp for use with a powered surgical handpiece comprises opposed proximal and distal ends and a rasp region. The proximal end includes a mount portion. The mount portion defines a pivot axis. The rasp region extends between the mount portion and the distal end and includes the distal end. The rasp region has opposed first and second surfaces connecting at a common edge. The first surface is convex and the second surface is concave. The rasp region has a plurality of cutting projections disposed on at least one of the first surface and the second surface. The rasp region has a center axis substantially parallel to the pivot axis.

The rasp and the features thereof may comprise additional features and modifications as set forth below, such features and modifications being included separately or in combination with each other, with such combinations being limited only by mutual exclusivity.

The mount portion may be substantially planar and may be substantially normal to the pivot axis.

The common edge may define a periphery of the rasp region that is any one of elliptical, ovate, obovate, lanceolate and oblanceolate.

The center axis of the rasp region may be substantially coincident with the pivot axis.

The rasp region may have a thickness T less than one third of an available distracted distance.

The rasp region may have cutting projections on both the first and second surfaces.

The rasp may have no cutting projections on the common edge.

A geometry of the rasp region may be derived from a database of measurement data.

The rasp region may have a shape of a wedge segment of a spheroid.

The wedge segment may have an included angle of less than 120 degrees.

A surgical tissue cutting system comprises a powered surgical handpiece and a rasp. The powered surgical handpiece comprises a body, a motor, and a mount. The motor is disposed inside the body. The mount defines a first pivot axis and is drivingly connected to the motor. The rasp is selectively removably connected to the mount. The rasp comprises opposed proximal and distal ends and a rasp region. The proximal end includes a mount portion. The mount portion defines a second pivot axis substantially coincident with the first pivot axis when the rasp is connected to the mount. The rasp region extends between the mount and the distal end and includes the distal end. The rasp region has opposed first and second surfaces connecting at a common edge with the first surface being convex and the second surface being concave. The rasp region has a plurality of cutting projections disposed on at least one of the first surface and the second surface. The rasp region has a center axis substantially parallel to the second pivot axis.

The surgical tissue cutting system and the components and features thereof may comprise additional features and modifications as set forth below, such features and modifications being included separately or in combination with each other, with such combinations being limited only by mutual exclusivity.

The mount portion may be substantially planar and may be substantially normal to the second pivot axis.

The common edge may define a periphery of the rasp region that is any one of elliptical, ovate, obovate, lanceolate and oblanceolate.

The center axis of the rasp region may be substantially coincident with the pivot axis.

The rasp region may have a thickness T less than one third of an available distracted distance.

The rasp region may have cutting projections on both the first and second surfaces.

The rasp may have no cutting projections on the common edge.

A geometry of the rasp region may be derived from a database of measurement data.

The rasp region may have a shape of a wedge segment of a spheroid.

The wedge segment may have an included angle of less than 120 degrees.

Relative orientations and directions (by way of example, distal, proximal, upper, lower, bottom, rearward, front, rear, back, outboard, inboard, inward, outward, lateral, left, right) are set forth in this description not as limitations, but for the convenience of the reader in picturing at least one embodiment of the structures described. Such exemplary orientations may be from the perspective of a user of a rasp system.

The elements shown may take many different forms and may include multiple and/or alternate components and facilities. The example components illustrated are not intended to be limiting. Indeed, additional or alternative components and/or implementations may be used. Further, the elements shown are not necessarily drawn to scale unless explicitly stated as such.

As illustrated in FIGS. 1-18, rasp systems 20, 20J, each an example of a surgical tissue cutting system 20, including any one of a plurality of example surgical rasps 22, 22A, 22B, 22C, 22D, 22E, 22F, 22G, 22H selectively removably mounted to an example powered surgical handpiece 24 or alternatively to an example alternative powered surgical handpiece 24J.

The powered surgical handpiece 24 may include a body 26, a motor 28 disposed within the body, and a mount 30 disposed at a distal end of the body 26. The mount 30 is drivingly connected to the motor 28 and may define a pivot axis 31. The handpiece 24 may be of the type used as an oscillating saw, including the type used to drive sagittal saw blades. The pivot axis 31 may be substantially normal to an orientation of the body 26. The handpiece 24 may have an example oscillation displacement range of five to eight degrees. An example commercially available powered surgical handpiece may be provided by a RemB™ Sagittal Saw handpiece by Stryker. The operation of such handpieces 24 is well known.

The example rasp 22 has a proximal end 32 with a mount portion 34 and extends to a distal end 36. The mount portion 34 may be substantially planar. With regard to the rasp 22, the words “proximal” and “distal” are used relative to the mount 30 when the rasp 22 is mounted therein. The mount portion 34 may define a rasp pivot axis 37 of the rasp 22. The rasp pivot axis 37 may be normal to the mount portion 34. When the rasp is mounted to the handpiece 24, the rasp pivot axis 37 may be coincident with the mount pivot axis 31. A rasp region 38 of the rasp 22 extends between the mount portion 34 and the distal end and includes the distal end 36 of the rasp 22. The rasp region 38 includes a first, or distal, surface 40 of the rasp. The rasp region 38 also includes a second, or proximal, surface 44 of the rasp, opposite the first surface 40. The surfaces 40 and 44 are curved. The first surface 40 may be convex and the second surface 44 may be concave. Either or both of the surfaces 40, 44 may have a plurality of cutting projections 46, by way of example, teeth. The surfaces 40 and 44 are described in more detail below.

The surfaces 40, 44 connect at a common edge 48 that defines a periphery 50 of the rasp region 38. The example rasp 22 does not include any cutting projection on the edge 48. The edge 48 may terminate at a tip 52 distal to the mount portion 34. The tip 52 may be pointed or may be blunt.

A clearance portion 53 may extend between and connect the mount portion 34 and the rasp region 38. The clearance portion 53 may extend substantially an axial length L1 of the mount 30 and may be substantially parallel to the pivot axis 37, that is, at substantially ninety degrees to the mount portion 34.

Figure 2:
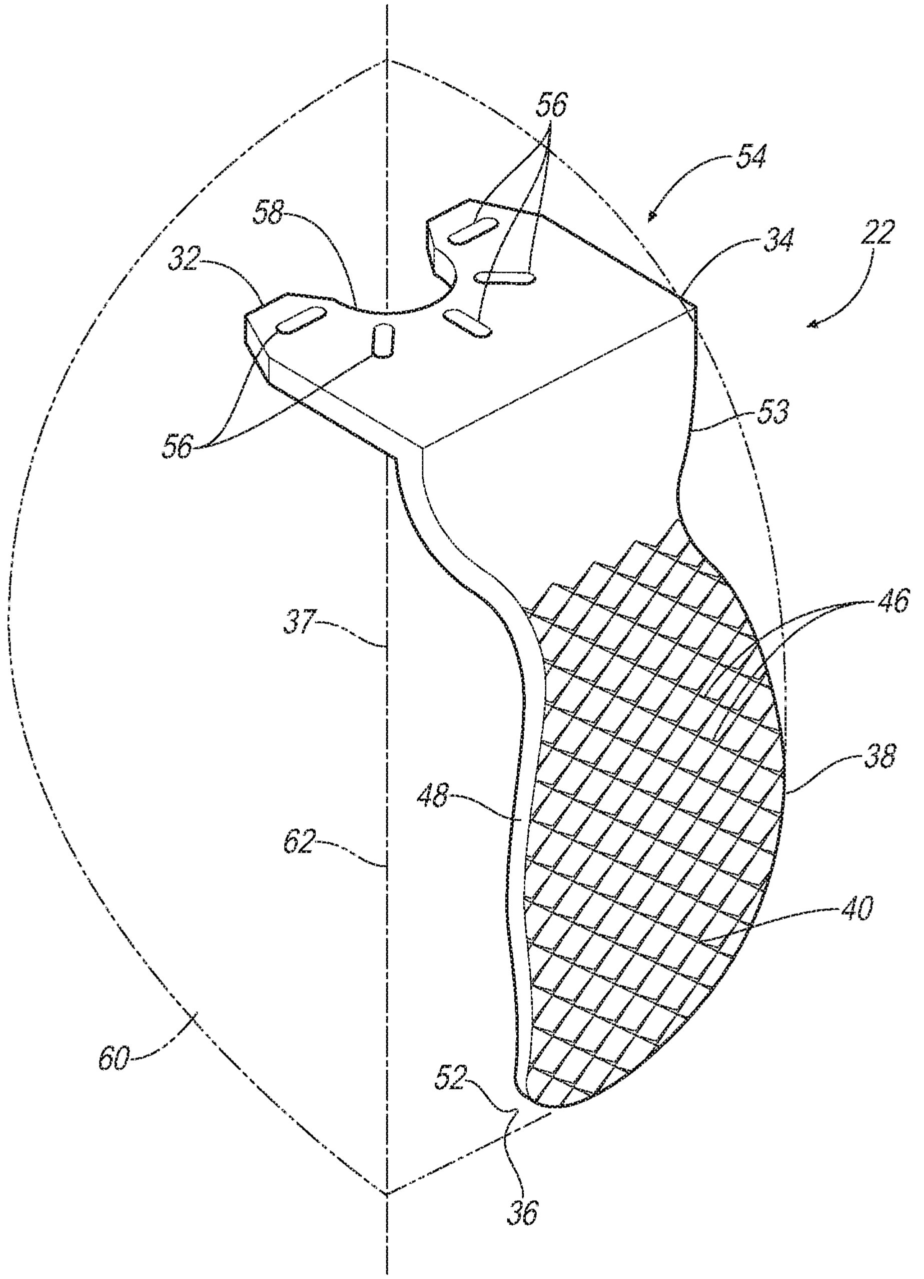
FIG. 2 is a perspective view of the example rasp of FIG. 1.
Figure 3:
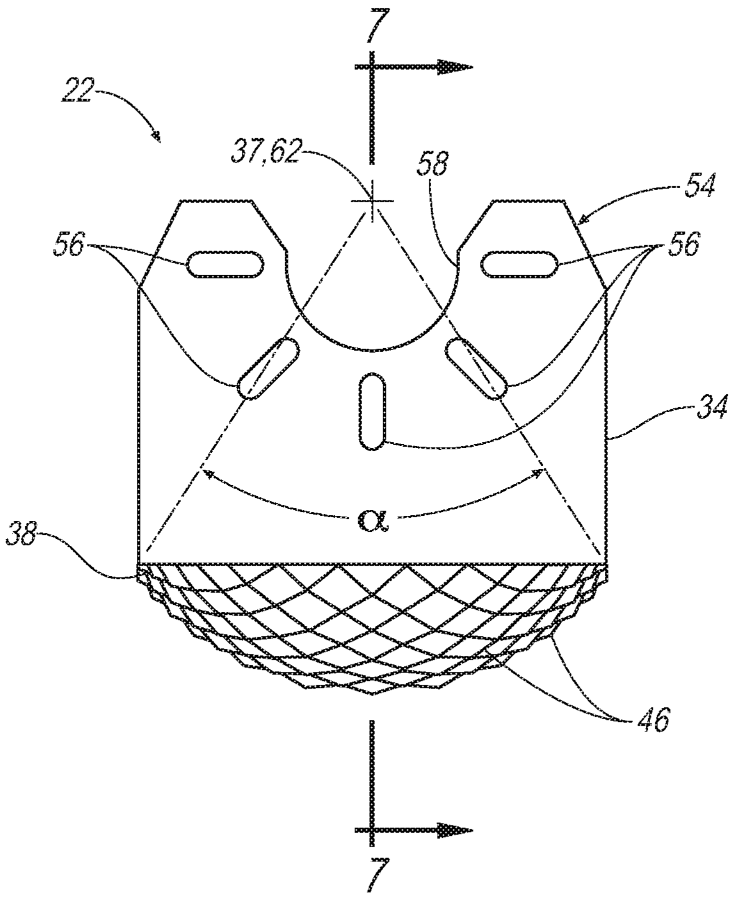
FIG. 3 is a top view of the example rasp of FIG. 1.

FIG. 2 and FIG. 3 show the mount portion 34 having one example form of a mount configuration 54 in which the mount portion 34 may be substantially flat and may include a plurality of receiving slots 56 and a center clearance notch 58. The mount portion 34 may be clamped by the mount 30. A spring, not shown, may be disposed within the mount 30 to provide a clamping force against the mount portion 34. One or more of the slots 56 may receive an engaging tine (not shown) of the mount 30. A wide variety of mount configurations are found in commercial use. While the inclusion of a mount portion 34 is necessary for the use of the presently disclosed rasp, the particular mount configuration selected is not critical to the disclosed rasp, so long as the mount configuration is compatible with the mount 30 of the handpiece 24 with which the rasp 22 is to be used.

Figure 4:
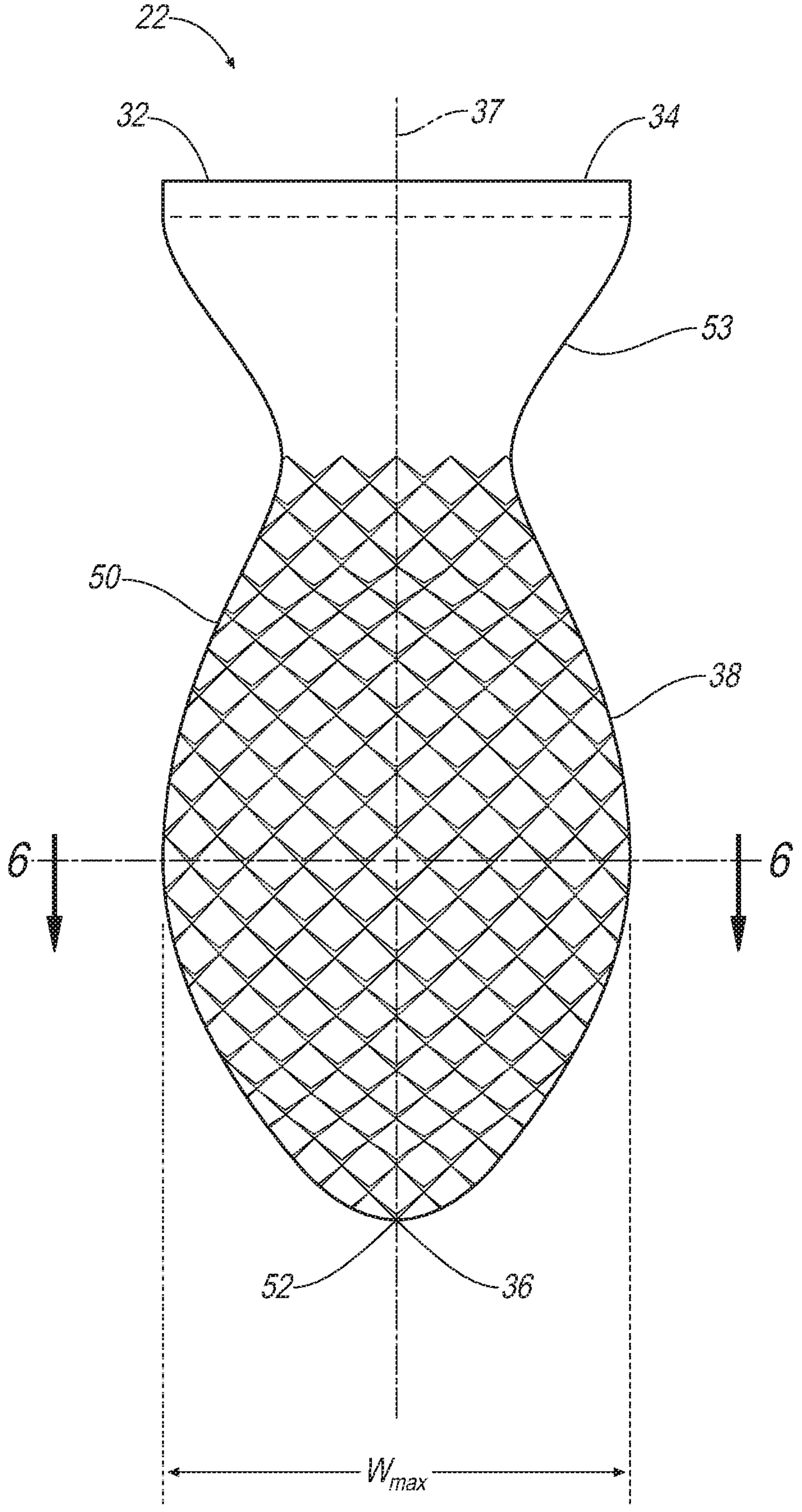
FIG. 4 is a front view of the example rasp of FIG. 1.

FIG. 4, a front view of the rasp 22, shows the example rasp region 38 may have what may be characterized as a leaf-like shape, or more particularly, an ovate shape. The rasp region 38 of the rasp 22 has a maximum width Wmax at a location between the mount portion 34 and the distal end 36. Additionally, the rasp region 38 may extend axially from the clearance portion 53. The clearance portion 53 may narrow, that is, neck down, as it extends away from the mount portion 34.

Figure 5:
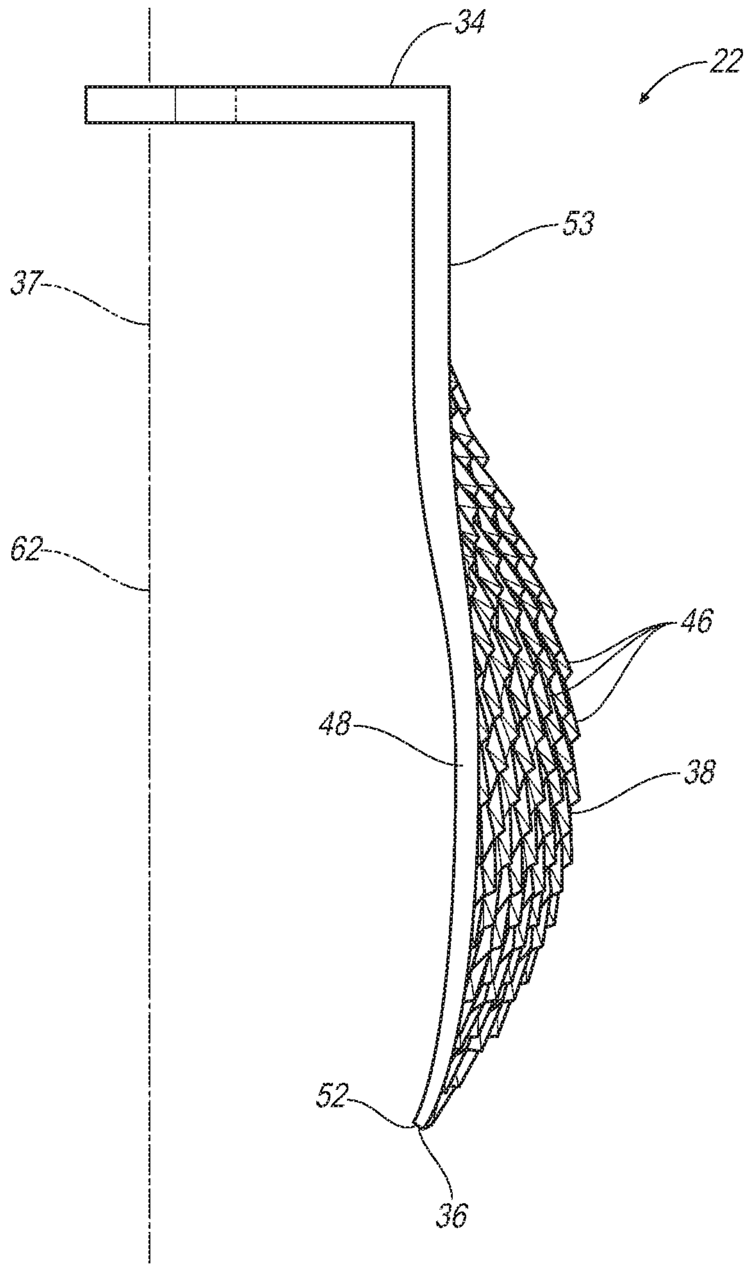
FIG. 5 is side view of the example rasp of FIG. 1.
Figure 7:
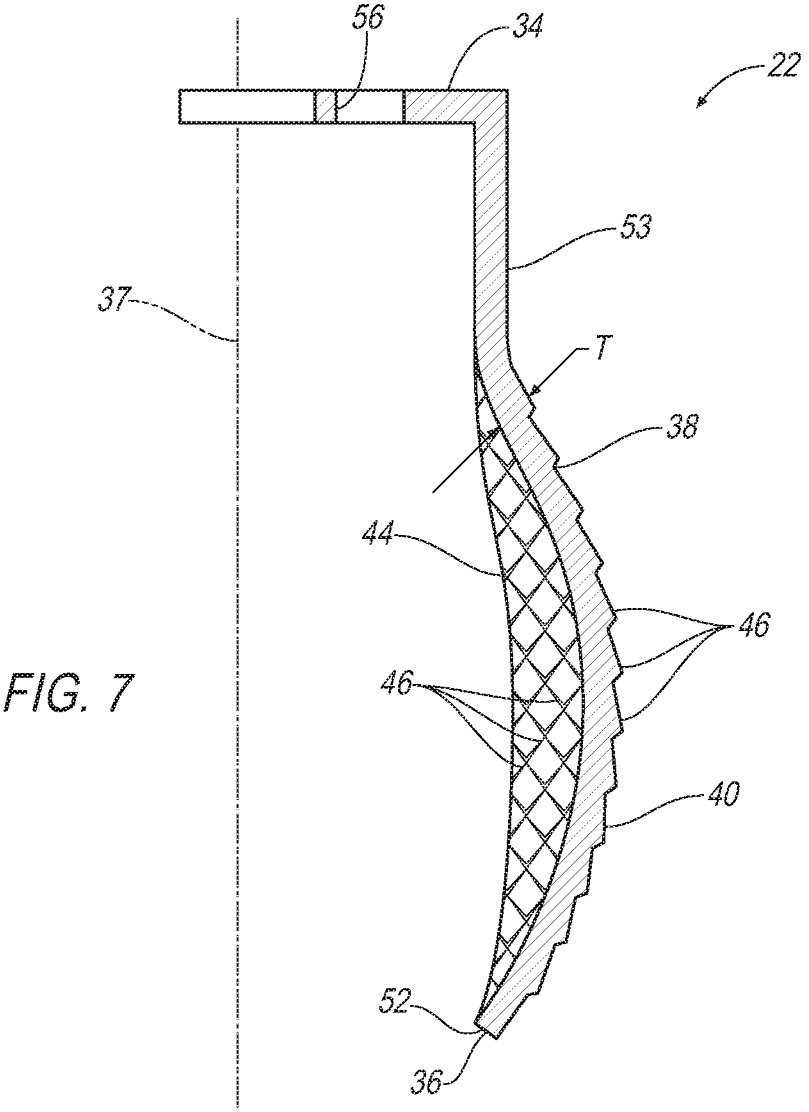
FIG. 7 is a side sectional view of the example rasp of FIG. 1 and FIG. 3 in the direction of arrows 7.

As shown in the side views of FIG. 5 and FIG. 7, the first surface and the second surface may arc away from the rasp pivot axis 37 to a predetermined point, and then may arc back toward the axis 37. The surfaces 40, 44 may each be continuous.

Figure 6:
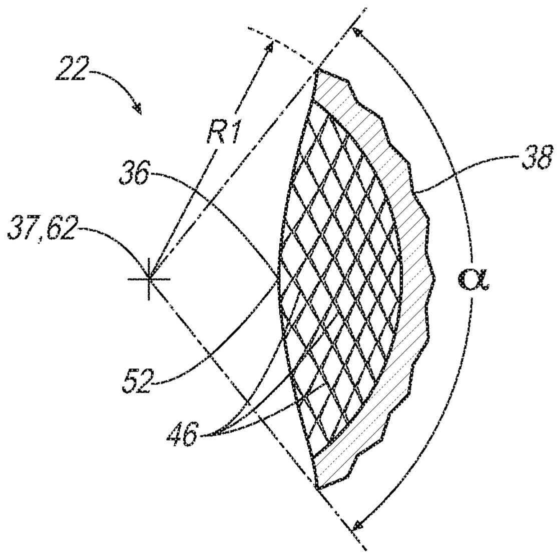
FIG. 6 is a top sectional view of the example rasp of FIG. 1 and FIG. 4 in the direction of arrows 6.

The surfaces 40, 44 may, as shown in FIG. 6, also arc about the rasp pivot axis 37. A distance R1 from the axis 37 to the second surface 44 may be of a constant radius for a given location on the axis 37.

Consistent with FIG. 7, the distance R1 may vary along the axis to provide the arc of FIG. 7. The rasp region 38 has opposed convex and concave surfaces 44, 40, beneficially allowing the rasp region 38 to be of a substantially constant thickness T as can be seen in FIG. 7. An example value of the thickness T may be 0.25 mm to 1.25 mm.

The surfaces 40, 44 may each be a section of a spheroid, by way of example and not limitation, any of a sphere, an ellipsoid, a prolate spheroid (like an American football), and an oblate spheroid. An example spheroid 60 is shown in phantom in FIG. 2. A center axis 62 of the spheroid 60, and of the surfaces 40,44 and the rasp region 38, may be substantially parallel to, and indeed may be coincident with or substantially coincident with, the rasp pivot axis 37. Substantially aligning the axes 37 and 62, as when the axes 37, 62 are substantially coincident, beneficially allows the rasp 22 to cut a complementary spheroidal shape in a work piece with a pivoting motion as described below. The surfaces 40, 44 may be centered on the rasp pivot axis 37. The term “substantially parallel to”, for the purpose of the relationship between the center axis 62 and the rasp pivot axis 37, may include angles of plus and minus 15 degrees from parallel. The greatest conformity of a resultant bone shape to a shape of the rasp surfaces 40 and 44 will occur with the axes 37 and 62 being parallel and coincident. The surfaces 40, 44 may be defined in part or in whole as a slice of a spheroidal form, as may be analogous to an outer surface of an orange segment, referenced to herein as a wedge segment in which the region 38 and the surfaces 40, 44 taper from narrow to the maximum width Wmax to narrower in the axial direction. An included angle $\alpha$ of the wedge segment may be less than 120 degrees. Restricting the angle α to a predetermined maximum value may beneficially allow the rasp 22 to be used in surgical sites in which space limitations may mitigate against the use of a larger rasp.

To define the rasp region 38, the above-referenced wedge segments may be truncated at either or each of the proximal and distal ends thereof. For example, the proximal end of the wedge may be truncated at the mount portion 34 or at the clearance portion 53 to allow the surfaces 40, 44 to be fixed at a desired distance from the rasp pivot axis 37. Similarly, the distal end of the wedge may be truncated at the tip 52 to facilitate insertion of the rasp 22 into a surgical site. Such truncation may contribute to the rasp region 38 having the above described leaf-like shape in the frontal viewing direction. Providing a spheroid shape that is not symmetrical about a mid-point of the axis 62, as for example if a top portion of a spheroid is a prolate spheroid, and the bottom portion is spherical, may also result in a rasp region 38 that presents a leaf-like shape in the frontal viewing direction.

The cutting projections 46 of the second surface 44 may be seen in each of FIG. 6 and FIG. 7. While the illustrated example rasp 22 has cutting projections 46 on each of the first surface 40 and the second surface 44, the rasp 22 may have cutting projections 46 on just one of the first surface 40 and the second surface 44.

The shape of the rasp region 38 for a particular rasp 22 may vary as may be best suited to a particular surgical application and to the size and shape of patients' bones. An anticipated range of size and shape may be established for particular bone joints. Such information may be from measurements established in clinical surveys, that is, measurement data, which may be aggregated in a database, of measurement data one example database being the Stryker Orthopaedic Modeling and Analytics ("SOMA") database. The database may be used to develop a family of rasp shapes and sizes, with each such rasp family member being configured to suit a particular range of bone sizes and shapes. FIG. 8 through FIG. 13 show front views of example alternative rasp regions. These examples are not to be taken as a comprehensive collection of alternative rasp region shapes, but as an illustration of some possible alternatives.

Figure 8:
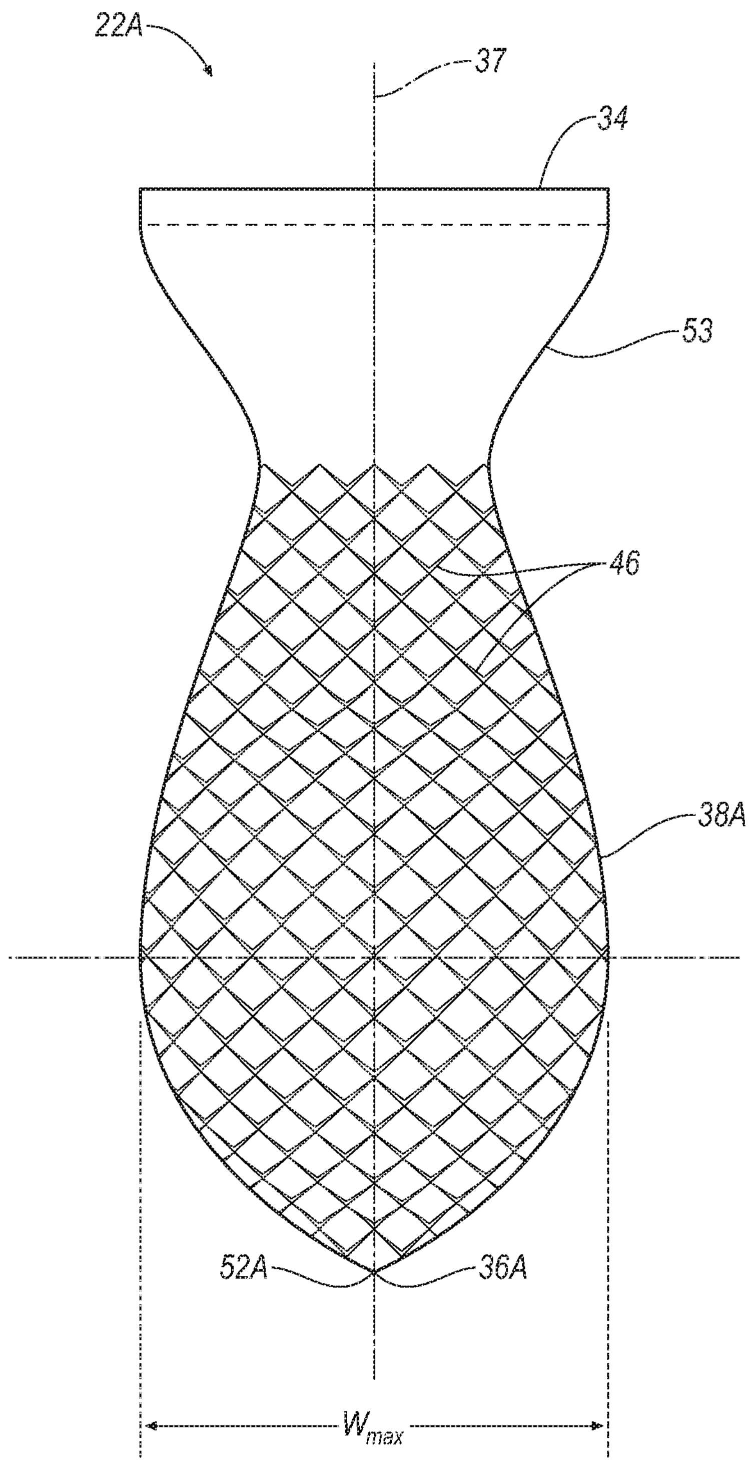
FIG. 8 is a front view of an example rasp having a second example shape.

The example rasp region 38A of FIG. 8 illustrates what may be characterized as an obovate shape with a pointed tip 52A at a distal end 36A of a rasp 22A.

Figure 9:
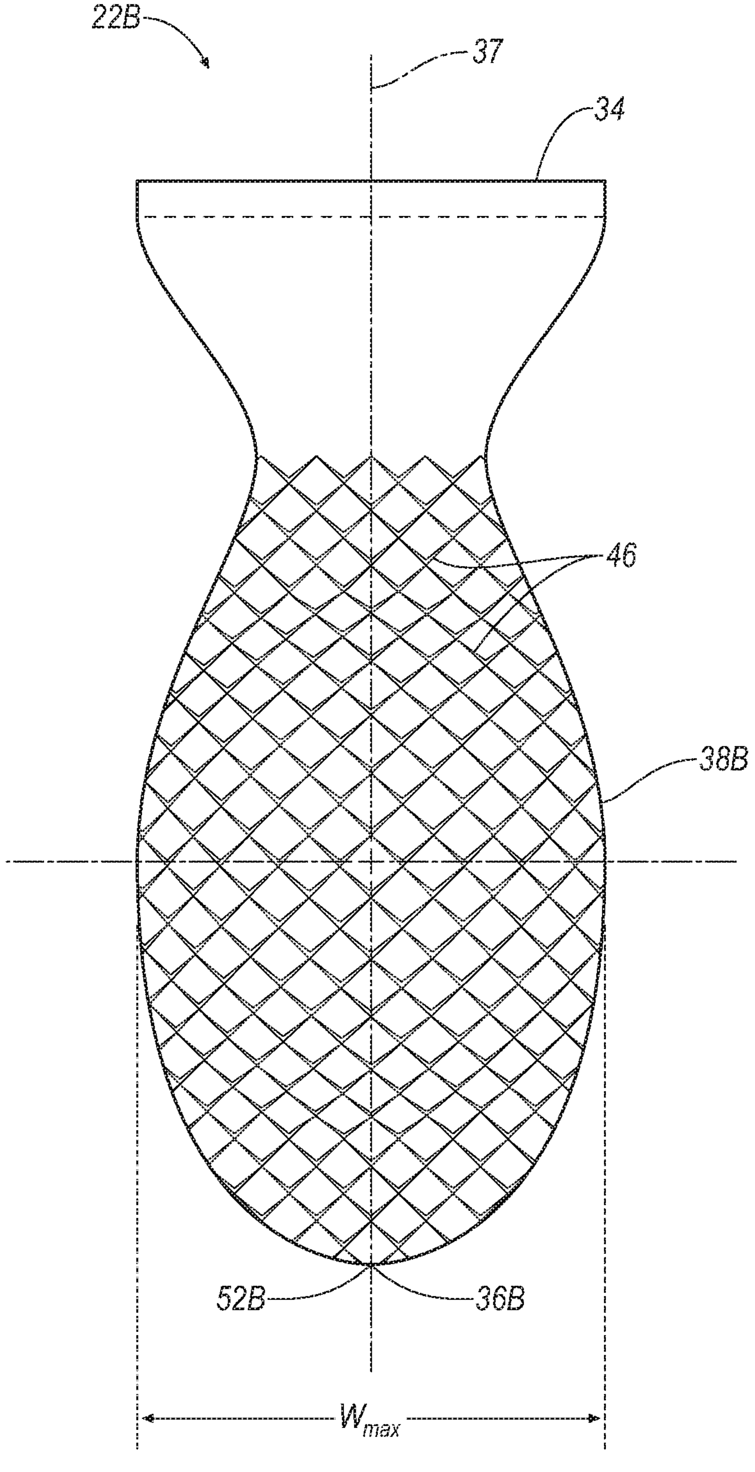
FIG. 9 is a front view of an example rasp having a third example shape.

The example rasp region 38B of FIG. 9 illustrates what may be characterized as an obovate shape with a rounded tip 52B at a distal end 36B of a rasp 22B.

Figure 10:
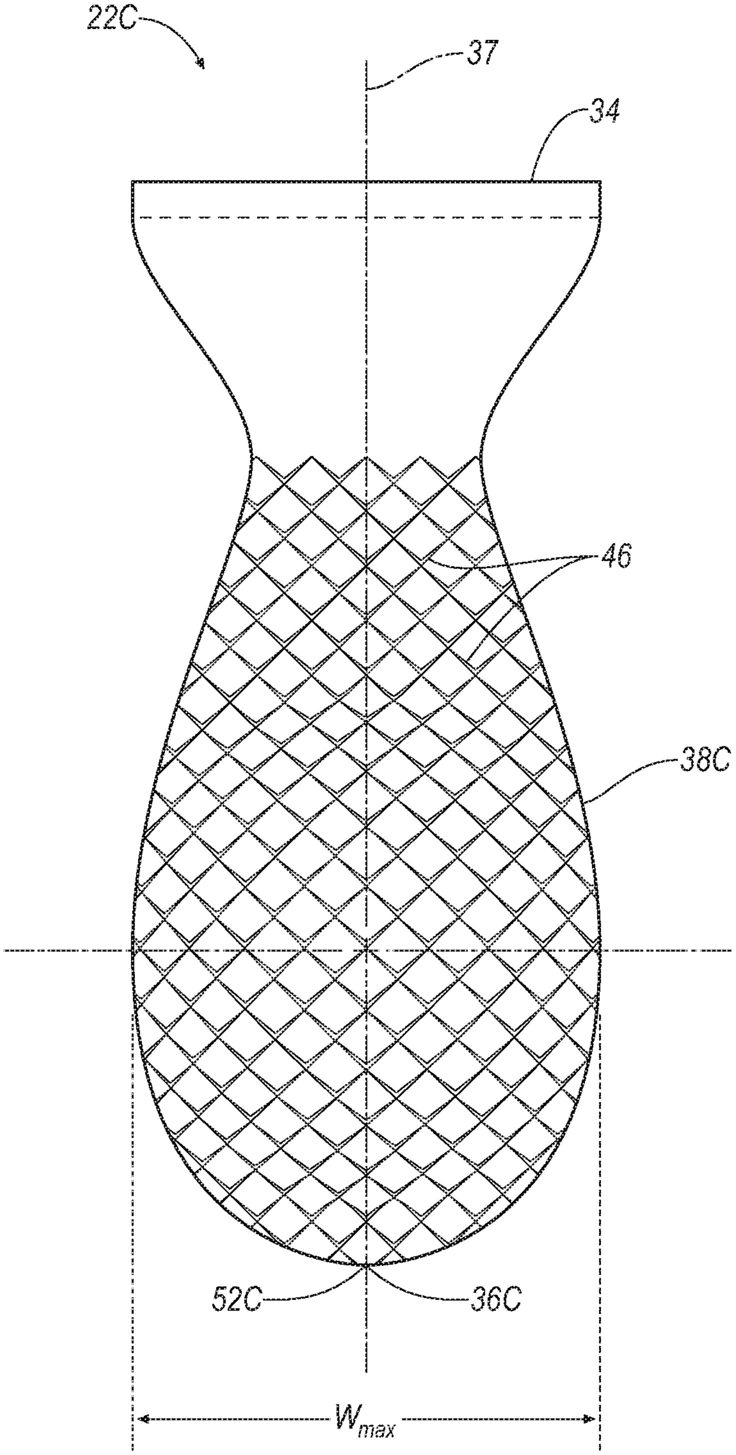
FIG. 10 is a front view of an example rasp having a fourth example shape.

The example rasp region 38C of FIG. 10 illustrates what may be characterized as an elliptical shape with a rounded tip 52C at a distal end 36C of a rasp 22C.

Figure 11:
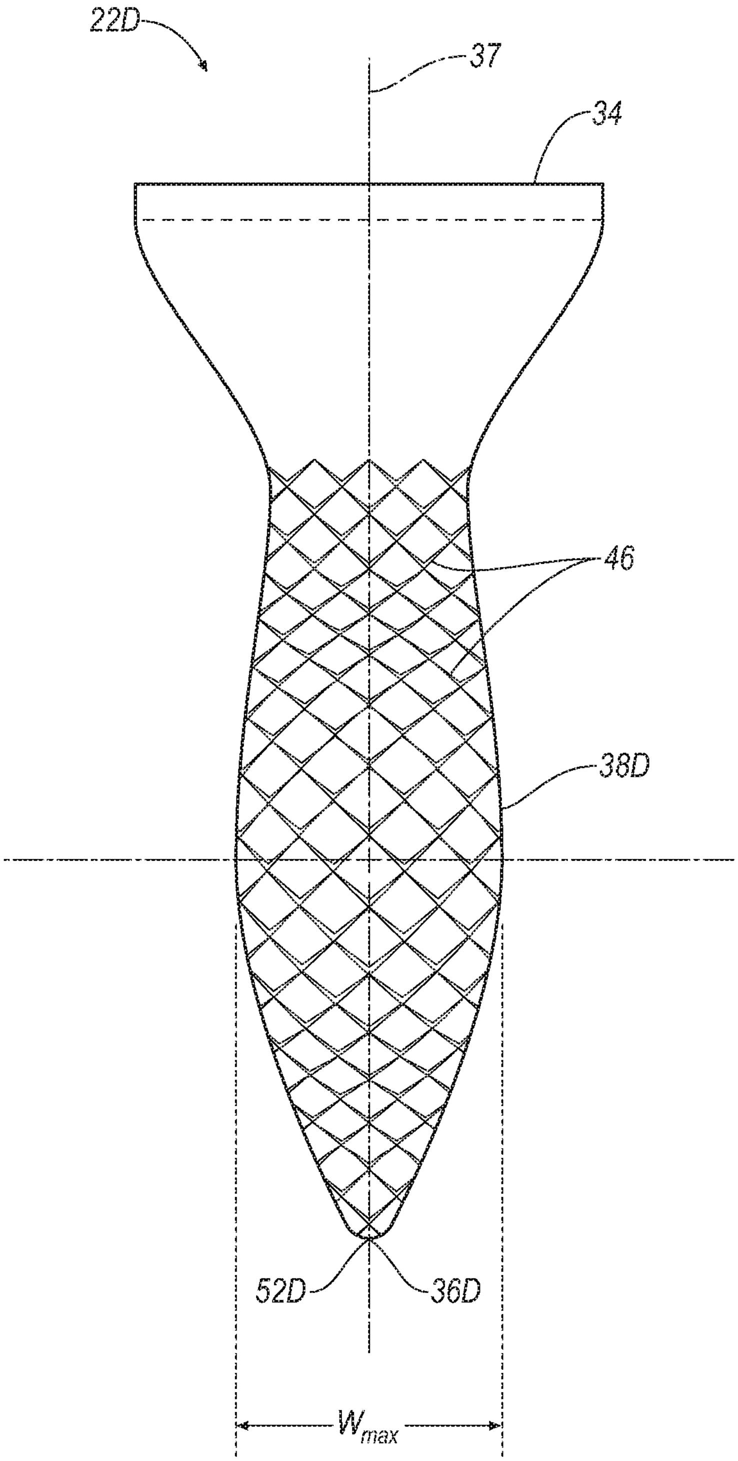
FIG. 11 is a front view of an example rasp having a fifth example shape.

The example rasp region 38D of FIG. 11 illustrates what may be characterized as a lanceolate shape with a rounded tip 52D at a distal end 36D of a rasp 22D.

Figure 12:
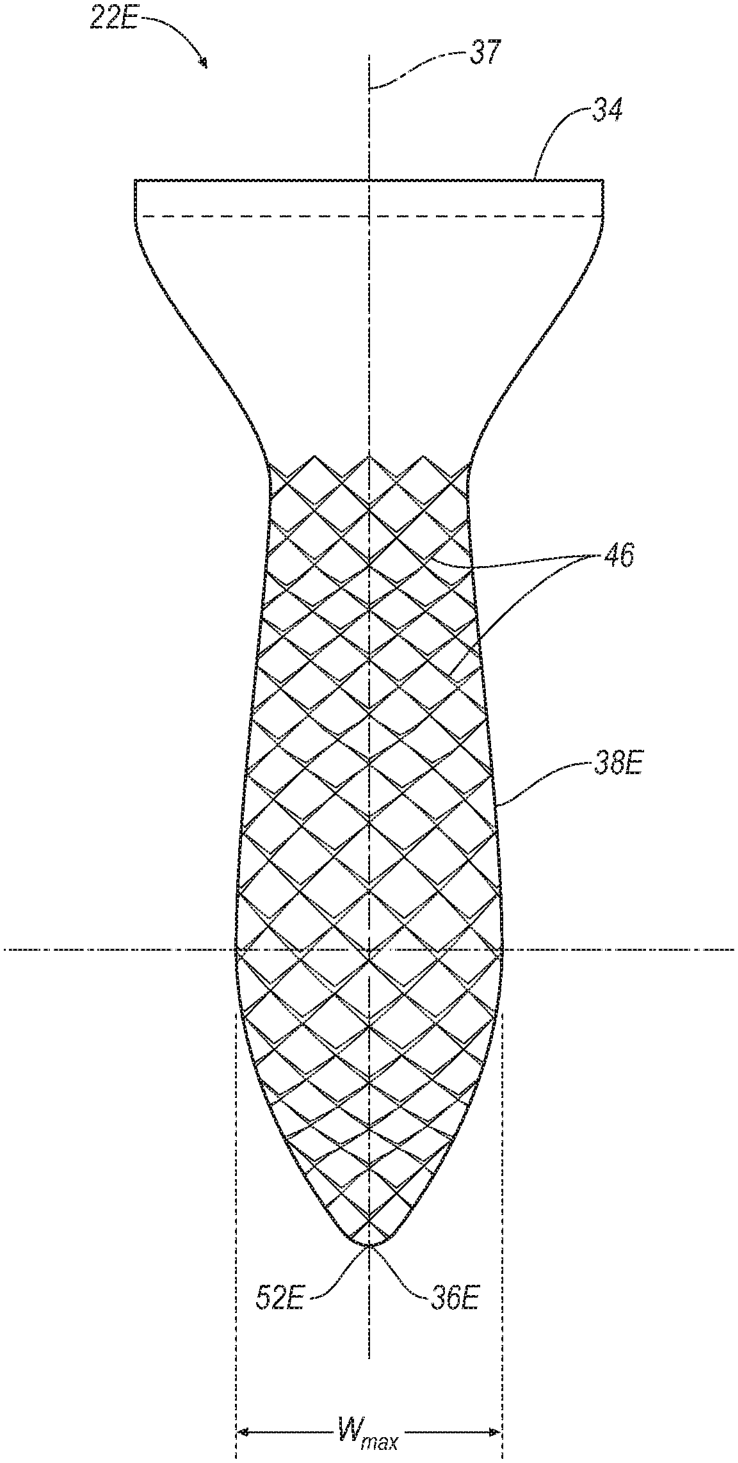
FIG. 12 is a front view of an example rasp having a sixth example shape.

The example rasp region 38E of FIG. 12 illustrates what may be characterized as an oblanceolate shape with a rounded tip 52E at a distal end 36E of a rasp 22E.

Figure 13:
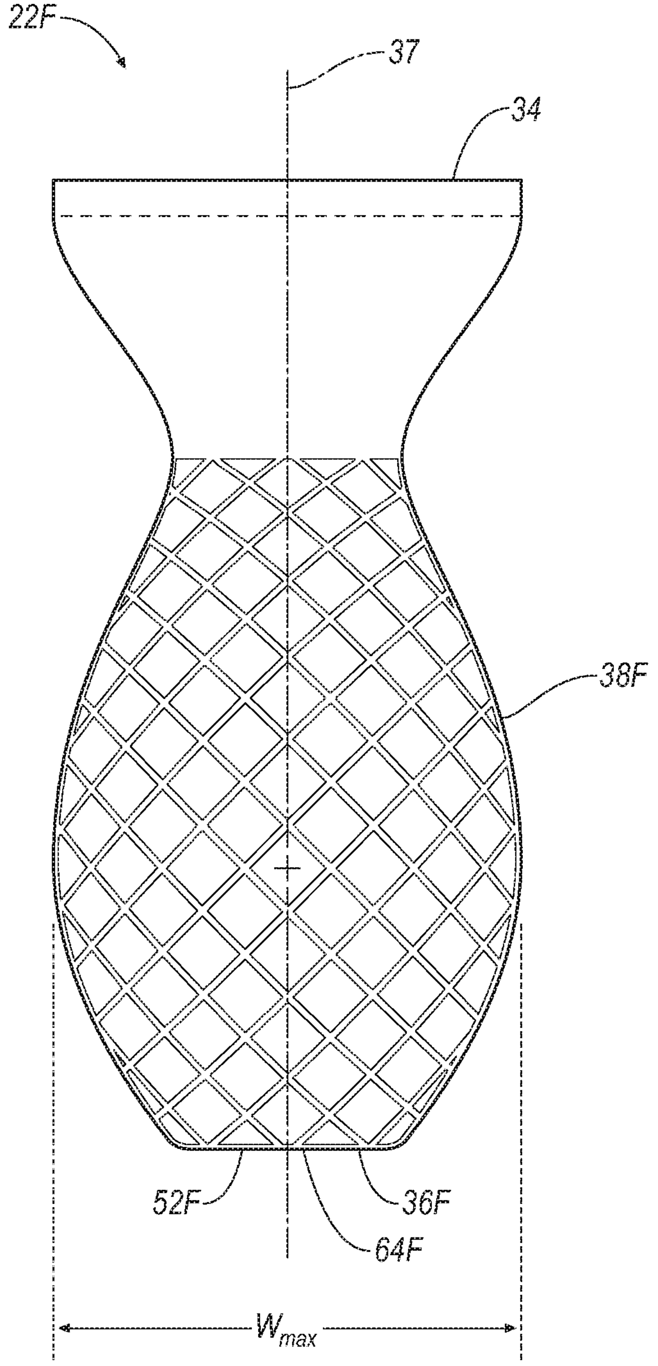
FIG. 13 is a front view of an example rasp having a seventh example shape.

The example rasp region 38F of FIG. 13 is substantially similar to that of the rasp region 38, but with a more blunted tip 52F, forming a plateau 64F at the distal end 36F of a rasp 22F.

Figure 14:
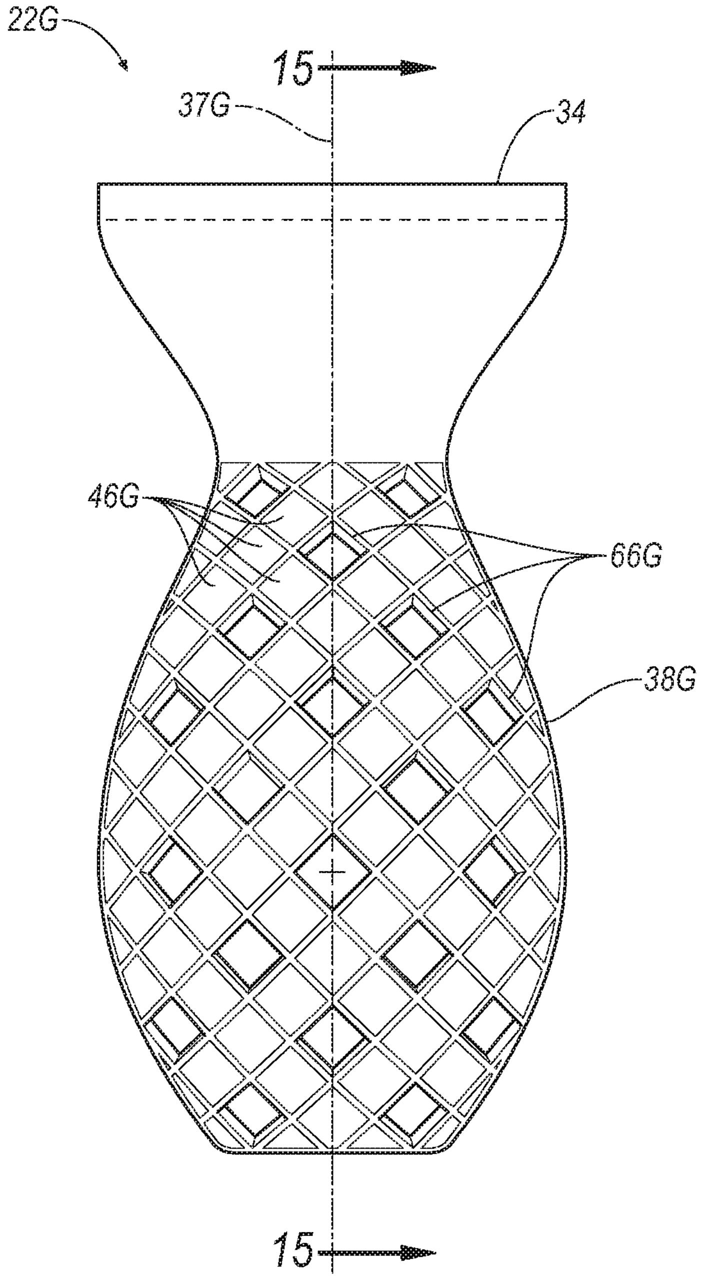
FIG. 14 is a front view of an example rasp having a plurality of debris transfer apertures.
Figure 15:
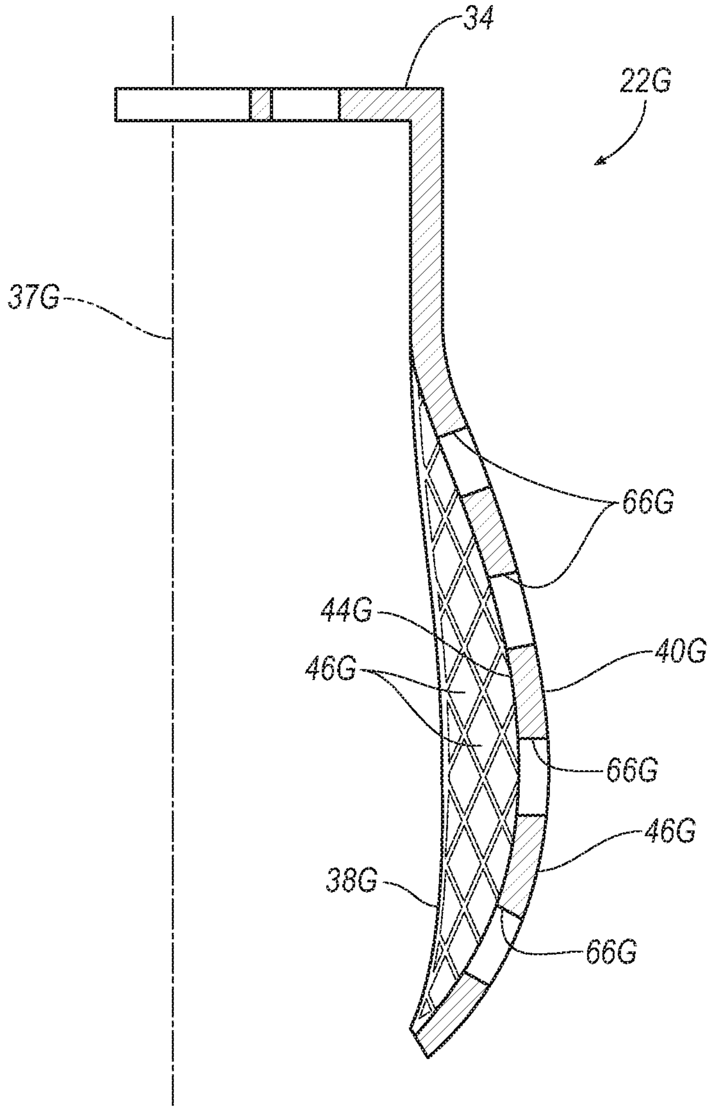
FIG. 15 is a sectional side view of the example rasp of FIG. 14 in the direction of arrows 15.

The example rasp region 38G of a rasp 22G with a rasp pivot axis 37G and shown in FIG. 14 and FIG. 15, is substantially similar to that of the rasp region 38F, but with a plurality of debris shedding apertures 66G for communicating debris therethrough. The debris shedding apertures 66G may prevent or slow cutting debris from building up on surfaces 40G, 44G and blocking the cutting projections 46G from removing additional material.

Figure 16:
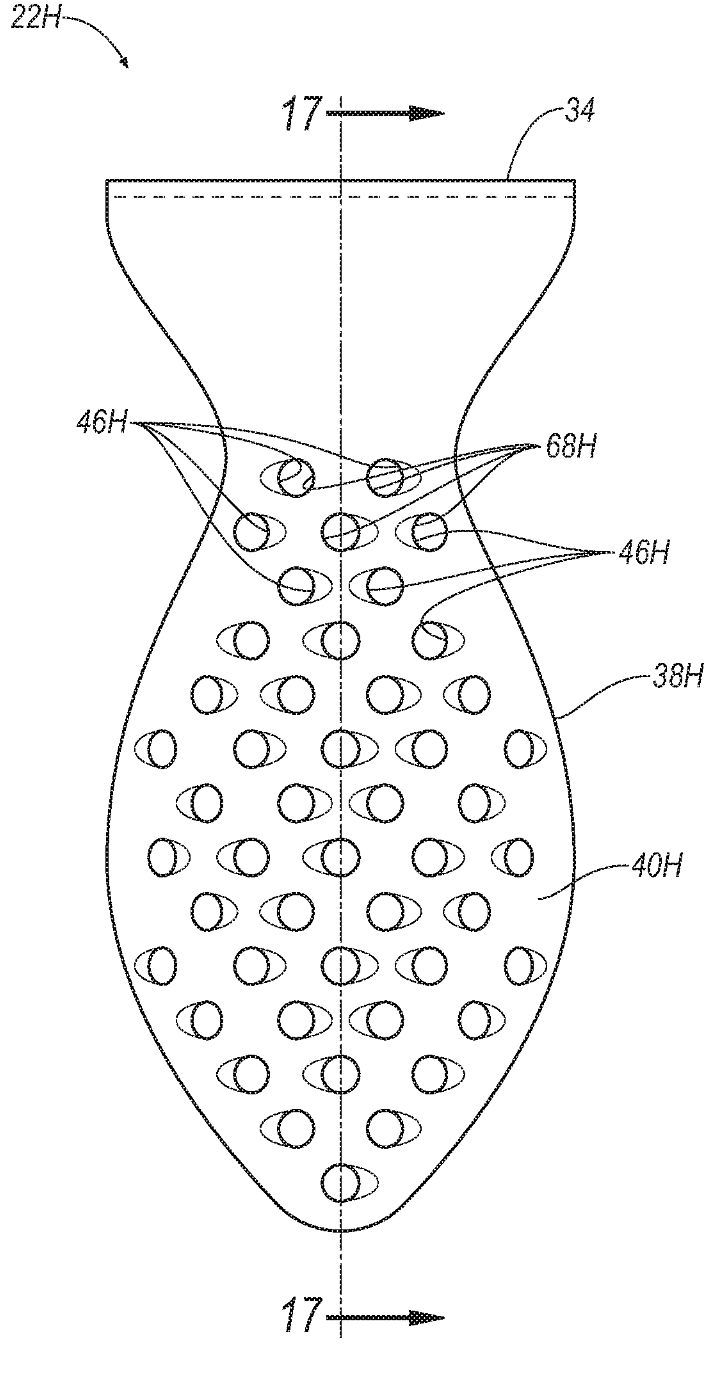
FIG. 16 is a front view of an example rasp with a grater configuration.
Figure 17:
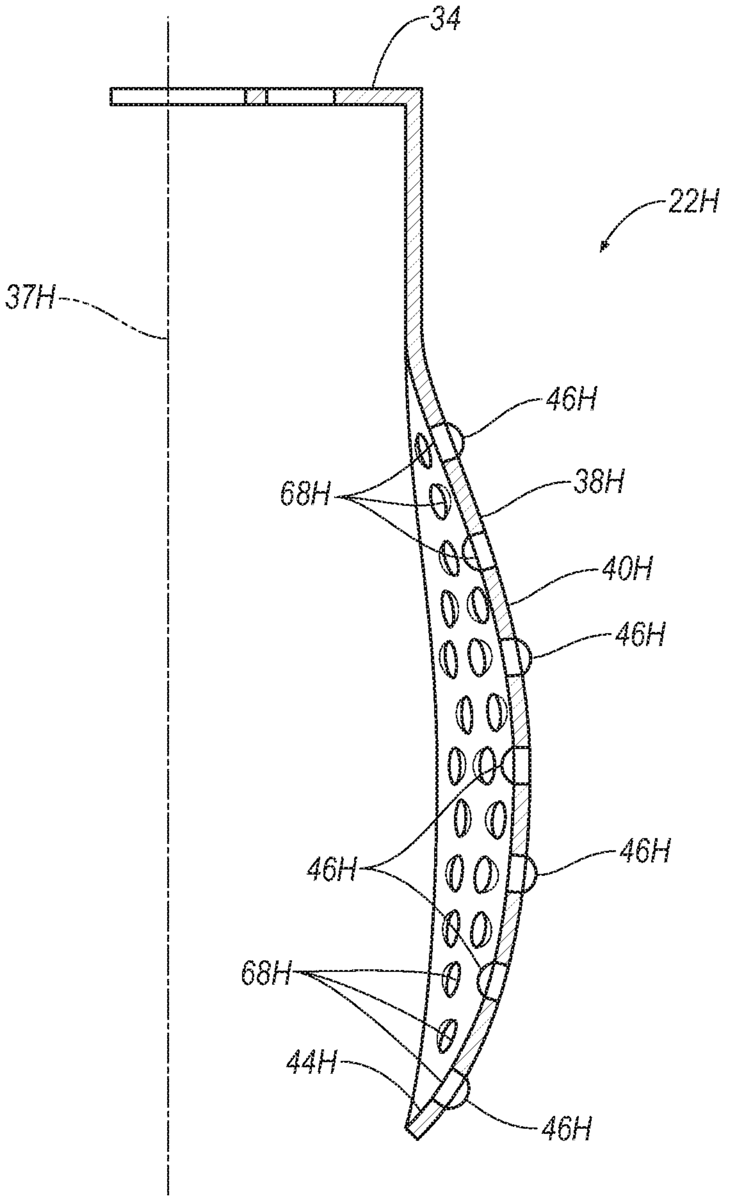
FIG. 17 is a sectional side view of the example rasp of FIG. 16.

The example rasp region 38H of an example rasp 22H having a rasp pivot axis 37H, shown in FIG. 16 and FIG. 17, is substantially similar to that of the rasp region 38A, but with a plurality of cutting projections 46H that may be defined at least in part by grating apertures 68H for shaving a working material, an example working material being bone. The cutting projections 46H may be formed in part by the cutting projections 46H being raised on a first side of the apertures in opposition to an anticipated direction of motion of the rasp 22H. The shape of the projections 46H may resemble blisters terminating at the apertures 68H, with the blisters having a razor edge at the apertures 68H. Certain of the projections 46H may be raised on a convex first surface 40H and others raised on a concave second surface 44H. Although not so illustrated, each aperture 68H could have two blister-type projections 46H on opposite sides of the aperture 68H, with a first of the projections 46H being on the first surface 40H, and the second of the projections 46H being on the second surface, so neither of the projections 46H at a particular aperture 68H blocks the other projection 46H. Having projections 46H on each of the first surface 40H and the second surface 44H allows the rasp region 38H to provide both concave and convex surfaces on the working material. The grating apertures 68H may communicate the shaved material of the working surface therethrough to avoid plugging the apertures 68H. The grating apertures 68H may prevent or slow cutting debris from building up on surfaces 40H, 44H and preventing cutting projections 46H from removing additional material. The grating projections 46H are illustrated as facing in alternate directions, for example to the left and to the right. Such an orientation allows material to be removed by the projections 46H in two directions of motion, for example, with pivoting to the left and to the right about the axis 37H. The projections 46H may alternatively face in a single direction, allowing material to be removed in just a single direction of pivoting motion about the axis 37H.

Figure 18:
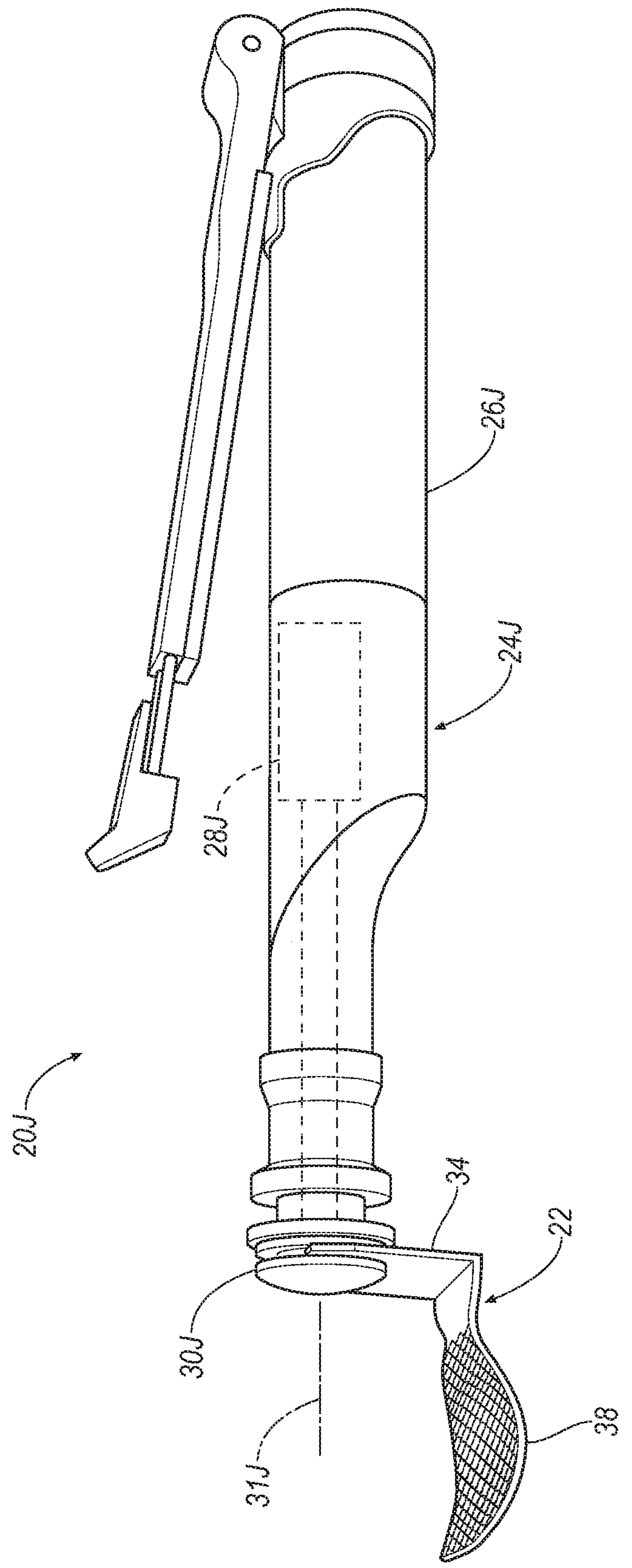
FIG. 18 is a side view of the example rasp of FIG. 13 mounted on a second example surgical handpiece.

The example alternative powered surgical handpiece 24J is illustrated in FIG. 18. The handpiece 24J may include a body 26J, a motor 28J disposed within the body 26J, and a mount 30J disposed at a distal end of the body 26J. The mount 30J is drivingly connected to the motor 28J and may define a pivot axis 31J. The handpiece 24J may be of the type used as an oscillating saw. The pivot axis 31J may be substantially parallel to an orientation of the body 26J. The handpiece 24J may have an example oscillation displacement range of five to eight degrees. By way of example and not limitation, the rasp 22 is shown as mounted to the handpiece 24J. An example commercially available powered surgical handpiece may be provided by a RemB™ Oscillating Saw handpiece by Stryker. The operation of such handpieces is well known.

In use, the rasp 22, 22A, 22B, 22C, 22D, 22E, 22F, 22G, 22H and the rasp system 20 may facilitate the fusing of bone joints, including, by way of example, fusing a metatarsophalangeal joint between two metatarsal bones of the foot. The rasp 22, or alternatively a rasp of similar configuration including but not limited to rasps 22A, 22B, 22C, 22D, 22E, 22F, 22G, 22H or equivalents thereof, all collectively referenced to hereafter in this description as the rasp 22, is selected based on a size and geometry of the bones of the joint. To facilitate access to the joint, a small incision may be made on a superior portion of the joint. The joint may then be distracted a small distance, an example distance being three to four millimeters. That the thickness T of the rasp region 38 is relatively thin, the previously cited example thickness being in an example range of between 0.25 mm and 1.25 mm, allows the rasp region 38 of the rasp 22 to be easily inserted into the available distracted distance of 3-4 mm. The rasp region may thus have a thickness T less than one third of an available distracted distance.

The selected rasp 22 may be inserted between the two metatarsal bones that are to be fused. To facilitate such insertion, the selected metatarsal bones may be distracted as noted above. The rasp 22 may then be inserted into the joint. The handpiece 24, 24J and more particularly, the handpiece motor 28, may then be actuated to oscillate the rasp 22. The spheroidal shapes of the rasp surfaces 40, 44 allows similar complementary shapes to be imparted to the bones. The forming of the complementary spheroidal shapes of the bones is greatly facilitated by the rasp 22 having the center axis 62 substantially coincident with the pivot axis 37. With the axes substantially coincident, an arc of displacement of a projection 46 will have a radius substantially equal to a distance of the projections 46 from the axis 62. The projections 46 will thus carve a portion of a spheroid in the bone having a radius of substantially the same distance, that is, substantially equal to a distance between the projection 46 and the axis 62. The first surface 40 of the rasp 22 may be pressed against an end of the first of the bones and oscillated to remove cartilage and to abrade the bone to reach the subchondral bone, or bleeding bone. The rasp 22 forms a concave surface on the end of the first of the bones. The second surface 44 of the rasp may be pressed against an end of the second of the bones to remove cartilage and the rasp 22 oscillated to abrade the bone to reach the subchondral bone, or bleeding bone, and to form a convex surface on the end of the second of the bones. The rasp 22 is withdrawn any surgical debris may be removed.

Providing a rasp 22 with projections on each of the first surface 40 and the second surface 44 beneficially allows the facing ends of both opposing bones to be formed without withdrawing the rasp from the incision. However, the ends of the bones could be similarly formed by using two separated rasps with cutting projections 46 on a single side in sequence. For example, a first rasp (not shown) having projections 46 on just the first surface 40 of the rasp may be inserted into the incision and pressed against an end of the first of the bones. The first rasp may be oscillated by the handpiece 24, 24J to remove cartilage and to abrade the bone. The first rasp thus forms a concave surface on the end of the first of the bones. The first rasp is withdrawn, and any surgical debris may be removed. A second rasp (not shown) having projections 46 on just the second surface 44 of the second rasp may be inserted in the incision and pressed against an end of the second of the bones. The second rasp may be oscillated by the handpiece 24, 24J to abrade the bone to form a convex surface on the end of the second of the bones. The second rasp is withdrawn, and any surgical debris may be removed.

The bones are pressed against each other. The concave surface of the first of the bones receives the convex surface of the second of the bones. The concave and convex surfaces formed by the rasp 22 are complementary and facilitate a final positioning of the bones with substantially complete contact therebetween. The concave and convex surfaces of the finished bone ends are substantially similar in shape to the original shape of the bone ends, minimizing the amount of bone that must be removed, and thus minimizing possible shortening of a combined length of the bones. The bones are positioned to a desired orientation and fixed in place to allow fusing. The incision is closed.

In the drawings, the same reference numbers indicate the same elements. Further, some or all of these elements could be changed. With regard to the media, processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A rasp for use with a powered surgical handpiece comprising:

opposed proximal and distal ends;

the proximal end including a mount portion with the mount portion defining a pivot axis; and a rasp region:

extending perpendicularly from the mount portion between the mount portion and the distal end and including the distal end, having opposed first and second surfaces connecting at a common edge with the first surface being convex and the second surface being concave, at least one of the first and second surfaces arcing away from the pivot axis and back toward the pivot axis in a reference plane that includes the pivot axis, and the common edge defining a periphery of the rasp region that is any one of elliptical, ovate, obovate, lanceolate and oblanceolate, having a plurality of cutting projections disposed on at least one of the first surface and the second surface, the cutting projections pivotable about the pivot axis, and having a center axis substantially parallel to the pivot axis.

2. The rasp of claim 1, wherein the mount portion is substantially planar and is substantially normal to the pivot axis.

3. The rasp of claim 1, wherein the rasp region has a thickness T less than one third of an available distracted distance.

4. The rasp of claim 1, wherein the rasp region has cutting projections on both the first and second surfaces.

5. The rasp of claim 1, wherein the rasp has no cutting projections on the common edge.

6. The rasp of claim 1, wherein a geometry of the rasp region is derived from a database of measurement data.

7. The rasp of claim 1, wherein the rasp region has a shape of a wedge segment of a spheroid.

8. The rasp of claim 7, wherein the wedge segment has an included angle of less than 120 degrees.

9. A surgical tissue cutting system comprising:

a powered surgical handpiece comprising:

a body, a motor disposed inside the body, and a mount defining a first pivot axis and drivingly connected to the motor; and a rasp selectively removably connected to the mount of the powered surgical handpiece, the rasp comprising:

opposed proximal and distal ends, the proximal end including a mount portion with the mount portion defining a second pivot axis substantially coincident with the first pivot axis when the rasp is connected to the mount, and a rasp region:

extending perpendicularly from the mount portion between the mount and the distal end and including the distal end, having opposed first and second surfaces connecting at a common edge with the first surface being convex and the second surface being concave, at least one of the first and second surfaces arcing away from the second pivot axis and back toward the second pivot axis in a reference plane that includes the pivot axis, the common edge defining a periphery of the rasp region that is any one of elliptical, ovate, obovate, lanceolate and oblanceolate, having a plurality of cutting projections disposed on at least one of the first surface and the second surface, the cutting projections pivotable about the second pivot axis, and having a center axis substantially parallel to the second pivot axis.

10. The system of claim 9, wherein the mount portion is substantially planar and is substantially normal to the second pivot axis.

11. The system of claim 9, wherein the rasp region has a thickness T less than one third of an available distracted distance.

12. The system of claim 9, wherein the rasp region has cutting projections on both the first and second surfaces.

13. The system of claim 9, wherein the rasp has no cutting projections on the common edge.

14. The system of claim 9, wherein a geometry of the rasp region is derived from a database of measurement data.

15. The system of claim 9, wherein the rasp region has a shape of a wedge segment of a spheroid.

16. The system of claim 15, wherein the wedge segment has an included angle of less than 120 degrees.

17. A rasp for use with a powered surgical handpiece comprising:

opposed proximal and distal ends extending along a pivot axis;

the proximal end including a mount portion being substantially planar and being substantially normal to the pivot axis; and a rasp region:

extending perpendicularly from the mount portion between the mount portion and the distal end and including the distal end, having opposed first and second surfaces connecting at a common edge with the first surface being convex and the second surface being concave, at least one of the first and second surfaces arcing away from the pivot axis and back toward the pivot axis in a reference plane that includes the pivot axis, the common edge defining a periphery of the rasp region that is any one of elliptical, ovate, obovate, lanceolate and oblanceolate, and having a plurality of cutting projections disposed on at least one of the first surface and the second surface.

18. The rasp of claim 17, wherein the first and second surfaces are centered on the pivot axis.

19. The rasp of claim 17, wherein the center axis of the rasp region is substantially coincident with the pivot axis.

* * * * *